United States Patent [19]

Görler et al.

[11] Patent Number: 4,835,178
[45] Date of Patent: May 30, 1989

[54] METHYLENDIOXYPHENATHRENE AND STILBEN DERIVATIVES, PROCESS FOR THE PREPARATION THEREOF, PHARMACEUTICAL COMPOSITIONS USING THESE, AND THERAPEUTIC APPLICATIONS

[75] Inventors: Klaus Görler, Bergisch Gladbach; Günter Krumbiegel, Bergheim-Quadrat; Michael Hanack, Tubingen; Lakshmina R. Subramanian, Gomaringen, all of Fed. Rep. of Germany

[73] Assignee: Dr. Madaus & Co., Cologne, Fed. Rep. of Germany

[21] Appl. No.: 171,695

[22] Filed: Mar. 22, 1988

Related U.S. Application Data

[62] Division of Ser. No. 900,823, Aug. 27, 1986, abandoned.

[30] Foreign Application Priority Data

Aug. 28, 1985 [DE] Fed. Rep. of Germany ....... 3530718

[51] Int. Cl.⁴ ............................................. A61K 31/36
[52] U.S. Cl. .................................. 514/463; 549/432; 549/436
[58] Field of Search ......................... 549/432; 514/463

[56] References Cited

FOREIGN PATENT DOCUMENTS 88030 11/1978 Poland .

OTHER PUBLICATIONS

Pakrashi et al., C.A., 90, 81,380g (1979).
Pakrashi et al., C.A., 90, 16746s (1979).
Mukhopadhyay et al., J. Nat. Products, 46, 507 (1983).

*Primary Examiner*—Nicky Chan
*Attorney, Agent, or Firm*—Felfe & Lynch

[57] ABSTRACT

The present invention provides compounds of the general formula:

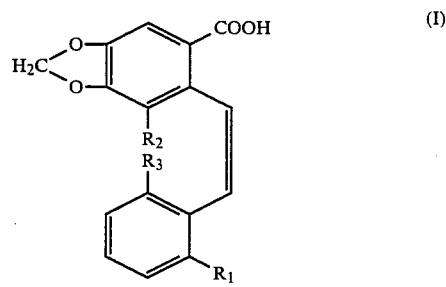

wherein $R_1$ is a hydrogen atom or a methoxy or ethoxy radical and $R_2$ and $R_3$ are hydrogen atoms or $R_2$ and $R_3$ together represent an aromatic carbon-carbon bond and $R_1$ is a hydrogen atom, a hydroxyl group or an ethoxy radical; and the pharmaceutically acceptable salts thereof.

The present invention also provides processes for the preparation of these compounds and pharmaceutical compositions containing them, as well as their use in therapy.

6 Claims, No Drawings

METHYLENDIOXYPHENATHRENE AND STILBEN DERIVATIVES, PROCESS FOR THE PREPARATION THEREOF, PHARMACEUTICAL COMPOSITIONS USING THESE, AND THERAPEUTIC APPLICATIONS

This is a divisional of application Ser. No. 900,823 filed Aug. 27, 1986, now abandoned.

The present invention is concerned with new methylenedioxyphenanthrene and stilbene derivatives, with processes for the preparation thereof and with pharmaceutical compositions containing them.

As immune-stimulating agents in the prophylaxis and therapy of infectious diseases, it is known to use aristolochic acids of the general formula:

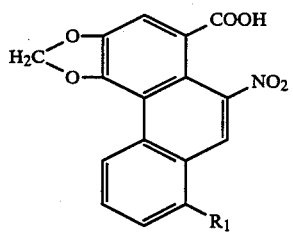

(II)

wherein $R_1$ is a hydrogen atom or a methoxy radical, these compounds manifesting a phagocytosis-increasing and antiviral action and increasing the success of healing in general infections. They have also been successfully used for the treatment of suppuration and ulcers.

However, in pharmacological investigations at higher dosage levels, there has recently been ascertained a cellular degeneration of the crop in rats so that a certain reservation appears to be necessary in the administration of these active materials which are very useful for purposes of treatment.

Surprisingly, we have now found that compounds of the general formula:

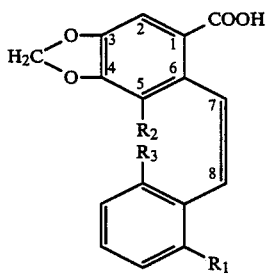

(I)

wherein $R_1$ is a hydrogen atom or a methoxy or ethoxy radical and $R_2$ and $R_3$ are both hydrogen atoms or together represent an aromatic carbon-cabon bond, in which case $R_1$ is a hydrogen atom, a hydroxyl group or an ethoxy radical, even at very high dosages (in comparison with the dosage usual in human therapy of 1 to 10 μg./kg.) in rats (10 mg./kg.), produced neither macroscopic nor histological indications of a squamous epithelial hyperplasia. Furthermore, no mutagenic effects were ascertained.

Consequently, the compounds of general formula (I) are very well suited for the prophylaxis and therapy of infectious diseases since they manifest a phagocytosis-increasing and antiviral action.

Of these compounds, 1-carboxy-3,4-methylenedioxy-8-methoxyphenanthrene is admittedly known (see J. Nat. Products, 46, 507 et seq./1983) of which it has been reported that at dosages of 90 mg./kg. it acts abortively in rabbits and at dosages of 60 mg./kg. it has an implanation-inhibiting action in mice. An immune-stimulating action thereof was not to have been assumed.

The compounds of general formula (I) can be prepared by reacting 6-bromopiperonyl bromide of the formula:

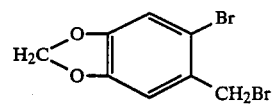

with triphenylphosphine in an anhydrous solvent to give a phosphonium salt of the formula:

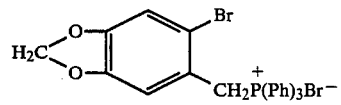

the latter compound being reacted with benzaldehyde, o-methoxybenzaldehyde or o-ethoxybenzaldehyde in the presence of a strong base to give a stilbene of the general formula:

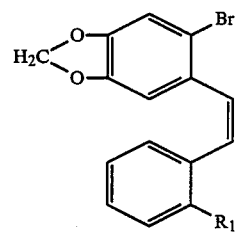

wherein $R_1$ is a hydrogen atom or a methoxy or ethoxy radical, this stilbene bromide either being converted with a metal cyanide, especially copper cyanide, in a polar aprotic solvent, especially in dimethylformamide, into the corresponding nitrile and this converted by hydrolysis into an acid of general formula (I) or the above stilbene bromide is converted with n-butyl lithium and carbon dioxide into an acid of general formula (I) or the above stilbene bromide is converted by ultraviolet irradiation into a phenanthrene derivative of general formula:

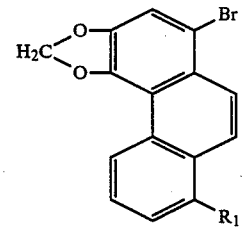

wherein $R_1$ is a hydrogen atom or a methoxy or ethoxy radical, and this compound is converted with a metal cyanide or with n-butyl lithium and carbonic acid in the above-mentioned manner into an acid of general formula (I) and, if desired, a compound of general formula (I), in which $R_1$ is a methoxy radical, is converted by ether splitting into a compound in which $R_1$ is a hydroxyl group; or a nitro compound of the general formula:

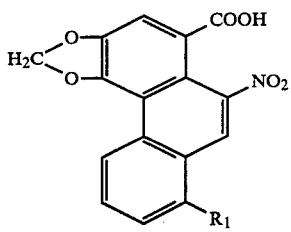

wherein $R_1$ is a hydrogen atom or a methoxy radical, is denitrated with a polysulphide to give a compound of general formula (I) and, when $R_1$ is a methoxy radical, if desired, this methoxy radical is changed into a hydroxyl group by ether splitting.

For the preparation of the above-mentioned 6-bromopiperonyl bromide, piperonyl alcohol is brominated in a lower alkyl carboxylic acid, preferably in acetic acid.

In the preparation of the phosphonium salt, as anhydrous solvent there is used, for example benzene or an alkylbenzene, preferably toluene or xylene.

In the case of the condensation of the phosphonium salt, as strong base there is used, for example, an alkali metal alcoholate, preferably lithium methylate. The stilbene thereby obtainable is present 85% in the Z-form and 15% in the E-form. The two isomers can be separated by treatment with diethyl ether, the trans-compound passing into the diethyl ether, whereas the desired cis-compound remains undissolved.

In the ultra-violet irradiation of the stilbene bromide, working is carried out, for example, in a solvent mixture of anhydrous tetrahydrofuran and anhydrous cyclohexane in a mixture ratio of, for example 1:12, with the addition of iodine and the introduction of nitrogen.

For the denitration, as polysulphide it is preferred to use ammonium polysulphide in weakly alkaline aqueous solution.

The 8-methoxy- and 8-ethoxyphenanthrene compounds ($R_2$ and $R_3$ together form an aromatic carbon-carbon bond and $R_1$ is a methoxy or ethoxy radical) can be converted by ether splitting into the corresponding 8-hydroxy compounds, for example by hydrolysis with pyridine hydrochloride.

The compounds according to the present invention can be used to increase the defence against infection. Thus, they bring about a significant activation of phagocytosis of leukocytes. Therefore, the compounds according to the present invention can be used for the treatment of general infections, for example by mycobacteria or pneumococci, and for the treatment of local infections. The compounds according to the present invention can also be used when a depression of phagocytosis is present, for example after the use of corticosteroids or sytostatics. By means of the use of the compounds according to the present invention, phagocytosis depression can again be normalized. Furthermore, we have also found an antiviral activity of the compounds of the present invention.

Therefore, the present invention also provides pharmaceutical compositions containing at least one compound of general formula (I) and/or at least one pharmaceutically acceptable salt thereof, in admixture with a pharmaceutically acceptable carrier.

The compounds according to the present invention have been investigated, inter alia, with regard to their macrophage-activating action. As parameter, there was used the stimulation of monocytes and macrophages in the peritoneal cavity of mice.

For the display of an increased chemotatic migration of monocytes into the peritoneal cavity and the differentiation of monocytes to macrophages with an increased ability to phagocytosis, an intraperitoneal administration of the test substances is preferable.

Stimulation is a process which requires a certain period of time. Therefore, the testing of the phagocytosis activity was taken as a conventional pharmacological model after a three day pretreatment of mice with compounds according to the present invention. In some test groups, immediately after administration of the test substance, the intraperitoneal cell population was removed in order to show that the observed stimulation only occurred after a certain incubation period.

SUBSTANCES AND MATERIALS

The substances to be tested were dissolved in water in an amount of 0.5 mg./ml. and, if required, diluted.

| ammonium chloride-tris buffer | |
|---|---|
| ammonium chloride | 8.3 g./liter |
| tris (tris-(hydroxymethyl)-aminomethane) | 4.119 g./200 ml. (pH 7.65) |
| mixing: 1 part of tris + 9 parts of ammonium chloride, adjusted to pH 7.2 with 2N hydrochloric acid | |
| PBS/BSA | |
| 40.0 g. sodium chloride | |
| 1.0 g. potassium chloride | make up to |
| 7.2 g. disodium hydrogen phosphate dihydrate | 5 liters with water (pH 7.4) |
| 1.0 g. monopotassium dihydrogen phosphate + | |
| 0.2 g. BSA (bovine serum albumin; Sigma Bo. A-9647) per 100 ml. PBS | |

DMEM

Dulbecco's modified Eagle medium with L-glutamine without phenol red (Gibco Cat. No. 041-1885) +5% FCS or +5% FCS+0.2% heparin

FCS

Foetal calf serum (Gibco Cat. No. 011-6290)

May-Grünwald solution

Modified (Merck Cat. No. 1424)

Sheep blood

No. 5, 30.08,84, MPI, Freiburg

Antiserum

Anti-sheep erythrocyte serum from rabbits No. 308, IKA 468/6-11 days; 18.07.78, MPI, Freiburg Experimentsl animals The investigations were carried out with 18 weeks old female hybrid mice (Balb/c×C57B16) F1. Before commencement of the experiments, the animals were adapted to the laboratory conditions for 5 days. They received pelleted standard feed for rats and mice (Altromin No. 1324) and tap water ad libitum. They were tested with a thioglycolate standard for three macrophage stimulatability and thereby showed good positive reactions.

Dosaging and administration

The substances were administered in aqueous solution (0.5 mg./ml.) in the following dosages:
intraperitoneal: 20 mcg./kg.
500 mcg./kg.
5 mg./kg.

The dilution of the parent solution for the administration of the various dosages amounted at

| 20 mcg./kg. | 1 mcg./ml. |
| 500 mcg./kg. | 25 mcg./ml. |
| 5 mg./kg. | 250 mcg./ml. | in each case 0.4 ml. thereof.

Administration scheme

1 Group=5 mice pretreatment: (a) 3 applications on 3 successive days; on the 4th day collection of the macrophages (b) an administration immediately before collecting the macrophages.

OBTAINING THE MACROPHAGE CELL SUSPENSION AND PHAGOCYTOSIS

Test principle

After administration of immunologically-activating substances, macrophages are stimulated in the experimental animals and monocytes induced for the differentiation into macrophages. The differentiated, stimulated macrophages, even after isolation, are also able to phagocytise in vitro with antigen structures opsonised with appropriate antibodies, in this case sheep erythrocytes. The phagocytised erythrocytes can be recognised microscopically.

Carrying out

After appropriate pretreatment, the mice are sacrificed by cervical vertebral fracture. The peritoneum is exposed and 4 ml. DMEM (5% foetal calf serum, 0.2% heparin) are administered intraperitoneally. After massage for about 30 seconds, 3 ml. of cell suspension are removed with a syringe and introduced into a polypropylene test tube in a cold bath (0° C.). From each test group, one mouse was used for the determination of the cell concentration in the exudate; there was adjusted a concentration of approximately $4 \times 10^5$ cells/ml.

Isolation of adherent macrophages

Macrophages and monocytes are selected from the isolated cell population by incubating them on covered glass dishes, macrophages and monocytes thereby adhering, whereas other cells do not. In tissue culture dishes with 24 cups (polystyrene, obtainable from Costar) are placed round covered glass dishes and covered with 0.25 ml. DMEM (with 5% foetal serum). For the uniform distribution of the cells, the dishes are placed on a shaker and into each batch there is pipetted, while shaking (2 minutes, about 200 r.p.m.), 0.25 ml. of cell suspension. Subsequently, the tissue culture dishes are incubated for 1 hour at 37° C. and with 8% carbon dioxide in an incubation cabinet. After the incubation, the non-adhering cells are sucked off and thereafter washed twice with 0.25 ml. amounts of DMEM (+5% foetal calf serum).

Opsonizing the sheep erythrocytes 1 ml. of sheep's blood is washed twice with 4 ml. PBS/BSA (centrifuging, 10 minutes at about 500 g). The washed blood is diluted 1:50 with PBS/BSA. The antiserum against sheep erythrocytes is diluted with PBS/BSA 1:200. Diluted sheep blood and diluted antiserum are mixed 1:1 and incubated for 1.5 hours with gentle shaking (about 80 r.p.m.).

Phagocytosis

Into each cup of the tissue culture dishes with adherent macrophages there is pipetted on to the covered glasses 0.5 ml. opsonized erythrocyte suspension. The dishes are incubated for 20 minutes at 37° C. with 8% carbon dioxide. Thereafter, excess erythrocytes are sucked off and the covered glasses washed twice with DMEM (0.5% FCS).

For the lysis of non-phagocytized erythrocytes, these are treated with, in each case, 1 ml. ammonium chloride-tris buffer (a period of action of 3.75 minutes is found to be suitable). After sucking off the buffer, the covered glasses are washed twice with PBS/BSA.

Phagocytosis representation (colour techniques)

After phagocytosis, macrophages are coloured according to Pappenheim's method using a combined May-Grünwald-Giemsa method. The coloration is carried out in the cups of the tissue culture dishes: 5 minutes May-Grünwald concentrated, suck off 3 minutes double distilled water adjusted with phosphoric acid min. 85% to pH 7.0; suck off 9 minutes Giemsa solution diluted 1:40 and filtered before use; suck off after-rinse with distilled water from a wash bottle.

After the coloration, the cell nuclei are red-violet and the cytoplasm bright blue. The phagocytized erythrocytes are recognisable as being pale pink. After air drying, the microscope preparations are securely stuck on to microscope slides with "Eukitt" (3 preparations/mouse).

Microscopic evaluation

Of the three microscope preparations of a mouse, two are selected. Use is made of a Zeiss microscope with 1000 fold enlargement and oil immersion. The third preparation is used if the result from the two preparations is not clear. Per preparation, there are counted 300 cells and, depending upon the phagocytosis activity, divided into classes with an increasing number of erythrocytes/macrophages.

| class | erythrocytes/macrophages |
| --- | --- |
| 1 | 0 |
| 2 | 1 |
| 3 | 2 |
| 4 | 3 |
| 5 | 4 |
| 6 | 5 |
| 7 | 6 |
| 8 | 7 |
| 9 | 8 |
| 10 | 9 |
| 11 | 10 |
| 12 | 11–20+ |

For the calculations, it is assumed that at 11 erythrocytes/MPH, the distribution in class 12 displayed a preponderance of 12 erythrocytes/macrophage. Macrophages of the 12th class occurred relatively infrequently Data preparation and graphic representation The counting of the microscopic preparations was carried out on a calculation device WANG LVP 2200 with a special application program which permitted a separate pick up of the classes. The averaging of the individual data is carried out with the program "MA 1", the graphic representation with the program "NPL", although other appropriate programs may be used as well.

The stimulation effect was illustrated for each test substance and dosage in two ways:

1. Division of the macrophages into the classes (erythrocytes/macrophages in %, (300 cells equal 100%). The number of macrophages which had not phagocytised any erythrocytes is also represented.

2. Division of the phagocytised erythrocytes (number of the NPH in one class x number of erythrocytes/MPH) into the classes in %, referred to the total number of the phagocytised erythrocytes as 100%. The number of macrophages which have not phagocytised any erythrocytes is disregarded in this case.

Parameters

As parameter of the macrophage stimulation, there is taken the increase of the phagocytosis activity, expressed as the number of phagocytised erythrocytes per macrophage (=class). A stimulation is shown by a decrease of the macrophages which had phagocytised none or few erythrocytes and by an increase of the macrophages with several erythrocytes.

Results

The MPH stimulation by 1-carboxy-3,4-methylenedioxy-8-methoxy phenanthrene, administered intraperitoneally, is shown in the accompanying drawings and the actual numerical results are shown in the following Tables, the MPH stimulation being that after 3 days ($\bar{x} \pm SEM$).

FIGS. 1(a) and 1(b) show the results obtained with $3 \times 20$ mcg/ml. i.p., FIG. 1(a) being the distribution of 300 cells into classes 1 to 12 in % and FIG. 1(b) being the distribution of phagocytised erythrocytes into classes 1 ro 12 in %.

FIGS. 2(a) and (b) show the corresponding results obtained with $3 \times 500$ mcg./ml. i.p.

FIGS. 3(a) and (b) show the corresponding results obtained with $3 \times 5$ mg./kg. i.p.

TABLE 1a

| n | class | mouse 1 | mouse 2 | mouse 3 | mouse 4 | $\bar{x}$ | SD | SE | MD |
|---|---|---|---|---|---|---|---|---|---|
| 1 | 1.00 | 75.67 | 71.33 | 66.50 | 72.17 | 71.417 | 3.777 | 1.889 | 71.750 |
| 2 | 2.00 | 12.67 | 17.00 | 20.00 | 15.50 | 16.292 | 3.056 | 1.528 | 16.250 |
| 3 | 3.00 | 6.83 | 6.17 | 8.67 | 7.67 | 7.333 | 1.080 | 0.540 | 7.250 |
| 4 | 4.00 | 2.17 | 3.33 | 3.50 | 2.50 | 2.875 | 0.644 | 0.322 | 2.917 |
| 5 | 5.00 | 0.67 | 1.67 | 1.17 | 1.17 | 1.167 | 0.408 | 0.204 | 1.167 |
| 6 | 6.00 | 1.33 | 0.17 | 0.17 | 0.17 | 0.458 | 0.583 | 0.292 | 0.167 |
| 7 | 7.00 | 0.17 | 0.33 | 0.00 | 0.50 | 0.250 | 0.215 | 0.108 | 0.250 |
| 8 | 8.00 | 0.00 | 0.00 | 0.00 | 0.17 | 0.042 | 0.083 | 0.042 | 0.000 |
| 9 | 9.00 | 0.17 | 0.00 | 0.00 | 0.00 | 0.042 | 0.083 | 0.042 | 0.000 |
| 10 | 10.00 | 0.00 | 0.00 | 0.00 | 0.00 | 0.000 | 0.000 | 0.000 | 0.000 |
| 11 | 11.00 | 0.33 | 0.00 | 0.00 | 0.17 | 0.125 | 0.160 | 0.080 | 0.083 |
| 12 | 12.00 | 0.00 | 0.00 | 0.00 | 0.00 | 0.000 | 0.000 | 0.000 | 0.000 |
| 1 | 1.00 | 0.0 | 0.0 | 0.0 | 0.0 | 0.00 | 0.00 | 0.00 | 0.00 |
| 2 | 2.00 | 26.5 | 34.8 | 37.5 | 31.2 | 32.50 | 4.77 | 2.38 | 33.01 |
| 3 | 3.00 | 28.6 | 25.3 | 32.5 | 30.9 | 29.30 | 3.14 | 1.57 | 29.72 |
| 4 | 4.00 | 13.6 | 20.5 | 19.7 | 15.1 | 17.21 | 3.39 | 1.69 | 17.39 |
| 5 | 5.00 | 5.6 | 13.7 | 8.8 | 9.4 | 9.34 | 3.32 | 1.66 | 9.07 |
| 6 | 6.00 | 13.9 | 1.7 | 1.6 | 1.7 | 4.72 | 6.14 | 3.07 | 1.69 |
| 7 | 7.00 | 2.1 | 4.1 | 0.0 | 6.0 | 3.06 | 2.60 | 1.30 | 3.09 |
| 8 | 8.00 | 0.0 | 0.0 | 0.0 | 2.3 | 0.59 | 1.17 | 0.59 | 0.00 |
| 9 | 9.00 | 2.8 | 0.0 | 0.0 | 0.0 | 0.70 | 1.39 | 0.70 | 0.00 |
| 10 | 10.00 | 0.0 | 0.0 | 0.0 | 0.0 | 0.00 | 0.00 | 0.00 | 0.00 |
| 11 | 11.00 | 7.0 | 0.0 | 0.0 | 3.4 | 2.58 | 3.33 | 1.66 | 1.68 |
| 12 | 12.00 | 0.0 | 0.0 | 0.0 | 0.0 | 0.00 | 0.00 | 0.00 | 0.00 |

TABLE 2a

| n | class | mouse 1 | mouse 2 | mouse 3 | mouse 4 | mouse 5 | $\bar{x}$ | SD | SE | MD |
|---|---|---|---|---|---|---|---|---|---|---|
| 1 | 1.00 | 63.00 | 52.83 | 53.83 | 47.33 | 51.33 | 53.667 | 5.775 | 2.583 | 52.833 |
| 2 | 2.00 | 13.00 | 19.67 | 20.50 | 17.83 | 15.67 | 17.333 | 3.053 | 1.365 | 17.833 |
| 3 | 3.00 | 8.00 | 11.83 | 13.33 | 16.00 | 12.17 | 12.267 | 2.893 | 1.294 | 12.167 |
| 4 | 4.00 | 5.00 | 6.00 | 5.83 | 7.83 | 8.67 | 6.667 | 1.523 | 0.681 | 6.000 |
| 5 | 5.00 | 4.33 | 3.83 | 3.00 | 5.00 | 5.50 | 4.333 | 0.979 | 0.438 | 4.333 |
| 6 | 6.00 | 2.83 | 2.83 | 1.33 | 2.50 | 2.67 | 2.433 | 0.630 | 0.282 | 2.667 |
| 7 | 7.00 | 1.17 | 1.33 | 0.83 | 1.17 | 2.17 | 1.333 | 0.500 | 0.224 | 1.167 |
| 8 | 8.00 | 0.83 | 0.50 | 0.50 | 0.83 | 0.50 | 0.633 | 0.183 | 0.082 | 0.500 |
| 9 | 9.00 | 1.17 | 0.67 | 0.17 | 1.00 | 0.67 | 0.733 | 0.384 | 0.172 | 0.667 |
| 10 | 10.00 | 0.00 | 0.17 | 0.33 | 0.00 | 0.00 | 0.100 | 0.149 | 0.067 | 0.000 |
| 11 | 11.00 | 0.67 | 0.33 | 0.17 | 0.50 | 0.50 | 0.433 | 0.190 | 0.085 | 0.500 |
| 12 | 12.00 | 0.00 | 0.00 | 0.17 | 0.00 | 0.17 | 0.067 | 0.091 | 0.041 | 0.000 |
| 1 | 1.00 | 0.0 | 0.0 | 0.0 | 0.0 | 0.0 | 0.00 | 0.00 | 0.00 | 0.00 |
| 2 | 2.00 | 12.5 | 17.5 | 20.3 | 13.5 | 11.9 | 15.13 | 3.60 | 1.61 | 13.54 |
| 3 | 3.00 | 15.3 | 21.0 | 26.4 | 24.3 | 18.5 | 21.11 | 4.41 | 1.97 | 21.04 |
| 4 | 4.00 | 14.4 | 16.0 | 17.3 | 17.8 | 19.8 | 17.06 | 2.02 | 0.90 | 17.30 |

TABLE 2a-continued

| n | class | mouse 1 | mouse 2 | mouse 3 | mouse 4 | mouse 5 | $\bar{x}$ | SD | SE | MD |
|---|---|---|---|---|---|---|---|---|---|---|
| 5 | 5.00 | 16.6 | 13.6 | 11.9 | 15.2 | 16.7 | 14.80 | 2.07 | 0.93 | 15.19 |
| 6 | 6.00 | 13.6 | 12.6 | 6.6 | 9.5 | 10.1 | 10.48 | 2.75 | 1.23 | 10.14 |
| 7 | 7.00 | 6.7 | 7.1 | 4.9 | 5.3 | 9.9 | 6.79 | 1.95 | 0.87 | 6.71 |
| 8 | 8.00 | 5.6 | 3.1 | 3.5 | 4.4 | 2.7 | 3.85 | 1.17 | 0.52 | 3.46 |
| 9 | 9.00 | 8.9 | 4.7 | 1.3 | 6.1 | 4.1 | 5.03 | 2.79 | 1.25 | 4.74 |
| 10 | 10.00 | 0.0 | 1.3 | 3.0 | 0.0 | 0.0 | 0.86 | 1.31 | 0.59 | 0.00 |
| 11 | 11.00 | 6.4 | 3.0 | 1.6 | 3.8 | 3.8 | 3.72 | 1.73 | 0.77 | 3.80 |
| 12 | 12.00 | 0.0 | 0.0 | 3.3 | 0.0 | 2.5 | 1.17 | 1.62 | 0.72 | 0.00 |

TABLE 3a

| n | class | mouse 1 | mouse 2 | mouse 3 | mouse 4 | mouse 5 | $\bar{x}$ | SD | SE | MD |
|---|---|---|---|---|---|---|---|---|---|---|
| 1 | 1.00 | 69.33 | 50.33 | 52.17 | 49.50 | 56.17 | 55.500 | 8.149 | 3.644 | 52.167 |
| 2 | 2.00 | 9.83 | 16.17 | 18.00 | 23.33 | 22.17 | 17.900 | 5.381 | 2.406 | 18.000 |
| 3 | 3.00 | 8.00 | 12.17 | 11.50 | 14.67 | 11.17 | 11.500 | 2.389 | 1.068 | 11.500 |
| 4 | 4.00 | 4.83 | 7.17 | 5.83 | 6.50 | 5.33 | 5.933 | 0.925 | 0.414 | 5.833 |
| 5 | 5.00 | 2.83 | 6.00 | 5.17 | 2.67 | 3.00 | 3.933 | 1.539 | 0.688 | 3.000 |
| 6 | 6.00 | 2.00 | 2.33 | 4.17 | 1.83 | 1.67 | 2.400 | 1.018 | 0.455 | 2.000 |
| 7 | 7.00 | 0.67 | 2.67 | 1.33 | 0.50 | 0.17 | 1.067 | 0.990 | 0.443 | 0.667 |
| 8 | 8.00 | 0.67 | 1.00 | 0.00 | 0.33 | 0.00 | 0.400 | 0.435 | 0.194 | 0.333 |
| 9 | 9.00 | 0.67 | 1.17 | 0.83 | 0.17 | 0.17 | 0.600 | 0.435 | 0.194 | 0.667 |
| 10 | 10.00 | 0.33 | 0.17 | 0.50 | 0.17 | 0.17 | 0.267 | 0.149 | 0.067 | 0.167 |
| 11 | 11.00 | 0.17 | 0.67 | 0.17 | 0.17 | 0.00 | 0.233 | 0.253 | 0.113 | 0.167 |
| 12 | 12.00 | 0.67 | 0.17 | 0.33 | 0.17 | 0.00 | 0.267 | 0.253 | 0.113 | 0.167 |
| 1 | 1.00 | 0.0 | 0.0 | 0.0 | 0.0 | 0.0 | 0.00 | 0.00 | 0.00 | 0.00 |
| 2 | 2.00 | 10.5 | 11.4 | 14.1 | 22.2 | 26.2 | 16.88 | 6.94 | 3.10 | 14.12 |
| 3 | 3.00 | 17.1 | 17.2 | 18.0 | 27.9 | 26.4 | 21.32 | 5.35 | 2.39 | 18.04 |
| 4 | 4.00 | 15.5 | 15.2 | 13.7 | 18.5 | 18.9 | 16.37 | 2.25 | 2.01 | 15.48 |
| 5 | 5.00 | 12.1 | 17.0 | 16.2 | 10.1 | 14.2 | 13.92 | 2.83 | 1.27 | 14.17 |
| 6 | 6.00 | 10.7 | 8.2 | 16.3 | 8.7 | 9.8 | 10.76 | 3.26 | 1.46 | 9.84 |
| 7 | 7.00 | 4.3 | 11.3 | 6.3 | 2.9 | 1.2 | 5.18 | 3.90 | 1.75 | 4.27 |
| 8 | 8.00 | 5.0 | 4.9 | 0.0 | 2.2 | 0.0 | 2.43 | 2.49 | 1.11 | 2.22 |
| 9 | 9.00 | 5.7 | 6.6 | 5.2 | 1.3 | 1.6 | 4.07 | 2.47 | 1.11 | 5.23 |
| 10 | 10.00 | 3.2 | 1.1 | 3.5 | 1.4 | 1.8 | 2.20 | 1.10 | 0.49 | 1.77 |
| 11 | 11.00 | 1.8 | 4.7 | 1.3 | 1.6 | 0.0 | 1.88 | 1.73 | 0.77 | 1.58 |
| 12 | 12.00 | 14.2 | 2.4 | 5.2 | 3.2 | 0.0 | 5.00 | 5.49 | 2.46 | 3.17 |

Dosage dependency of the stimulation effect

The control group, after intraperitoneal or oral administration of physiological sodium chloride solution, shows that the intraperitoneal administration itself brings about a weak macrophage activation, a high proportion of the macrophages having phagocytized two erythrocytes.

Consequently, an increase of the macrophages with more than two erythrocytes is to be interpreted as being a substance effect. Therefore, the % sum of the erythrocytes above the 4th class (macrophages with 3 or more erythrocytes) is placed in relationship to the dosage.

FIG. 4 of the accompanying drawings shows the dependency of the % sum of erythrocytes from the 4th class and above upon the dosage after intraperitoneal administration of 20 mcg./kg., 500 mcg./kg. and 5 mg./kg. The control is at 45%±6% ($\bar{x}$±SEM). In FIG. 4, the range ±SEM around the average value is shown by the broken line.

The following Table 4 shows the dosage dependency of the macrophage stimulation after intraperitoneal administration, x being the dosage (mcg./kg.), y the % sum of the phagocytised erythrocytes and SE the standard error of the means:

TABLE 4

| No. | x value | y value | SE value | M |
|---|---|---|---|---|
| 1 | 20.000 | 38.2000 | 2.7800 | 4 |
| 2 | 500.000 | 63.7600 | 3.3200 | 5 |
| 3 | 5000.000 | 61.8000 | 5.4200 | 5 |

Evaluation

The substances bring about an increase of the macrophage activation of 38% at 20 mcg./kg. and of 64% at 500 mcg./kg., a further increase of the dosage to 5 mg./kg. resulting in a slight weakening of the stimulation. In the selected dosage range, the macrophage activation does not run linearly.

The test group which had been treated once intraperitoneally directly before obtaining the macrophages demonstrated that the observed effects only occur after an incubation period. This finding indicates that the substance in vivo induces the mechanisms in the macrophages responsible for the phagocytosis increase. This points to the following effects:

1. stimulation of the membrane internalising rate
2. increase of the Fc receptor density and/or
3. increase of the mobility of the C3B receptors.

The other compounds according to the present invention show a comparable pharmacological action. The action was confirmed with other pharmacological models and also clinically.

The following Examples are given for the purpose of illustrating the preparation of the compound of the present invention:

EXAMPLE 1

1-Carboxy-3,4-methylenedioxy-2'-methoxystilbene (a) Preparation of 6-bromopiperonyl bromide

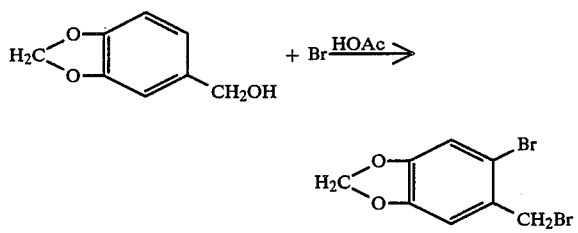

120 g. Piperonyl alcohol in 240 g. acetic acid is placed in a 1 liter three-necked flask equipped with a dropping funnel, drying tube and internal thermometer and cooled in an ice bath. 48 ml. bromine dissolved in 120 ml. acetic acid is slowly added dropwise to this solution, while stirring, so that the temperature remained between 15° and 25° C. The reaction mixture is left to stand overnight and the precipitated crystals are filtered off with suction, washed with water and recrystallized from methanol; m.p. 92°–93° C. Yield 174 g. (75% of theory).

(b) Preparation of the triphenylphosphonium salt

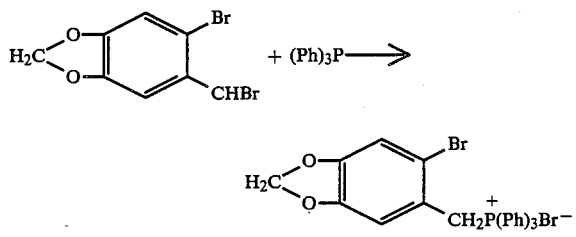

294 g. 6-bromopiperonyl bromide and 262 g. triphenylphosphine are placed in a 3 liter three-necked flask equipped with a reflux condenser and KPG stirrer and dissolved in anhydrous toluene, while stirring. The reaction mixture is heated for 2 hours, while stirring, and then further stirred for 24 hours at ambient temperature. The triphenylphosphonium salt formed is filtered off with suction, washed with a little toluene and dried in a desiccator. The yield is 500 g. (95% of theory).

(c) Preparation of the stilbene derivative

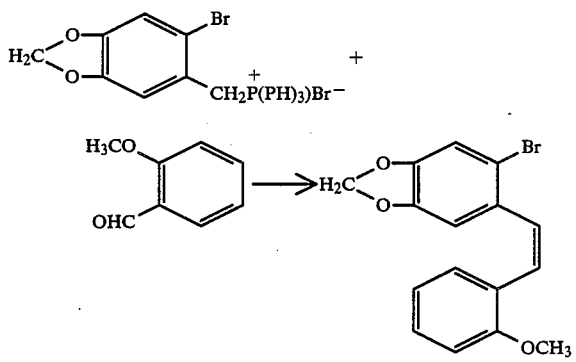

0.98 g. (0.14 g. atom) of lithium wire cut up into small pieces are added, under an atmosphere of nitrogen, to 30 ml. anhydrous methanol. When the reaction is finished (observed optically) the solution obtained is added dropwise, while stirring, in the course of 2.5 hours at 90° C. to a solution of 76.96 g. (0.14 mole) of the above triphenylphosphonium salt and 17.68 g. (0.13 mole) o-anisaldehyde, dissolved in 200 ml. anhydrous dimethylformamide. The reaction solution is stirred for a further hour at 90° C. After cooling to ambient temperature, the reaction mixture is poured into 700 ml. water and the precipitate obtained is filtered off and dried.

The dried product is extracted in a Soxhlet apparatus with petroleum ether (b.p. 30° to 50° C.) until the residue in the collar no longer contains any stilbene (TLC; silica gel; dichloromethane). The petroleum ether is evaporated in a vacuum and the residue obtained (64.82 g. of mixture) is recrystallized from ethanol, the greater part of the impurities and of the unreacted product hereby being separated off. The 31.13 g. of precipitate obtained are slurried in 300 ml. diethyl ether and boiled for 2 hours to separate the cis and trans mixture. After cooling, the solid material is filtered off and dried. Yield: 23.87 g. (52% of theory) of the pure cis compound (tested by TLC and NMR); m.p. 112° C.

(d) Preparation of 1-cyano-3,3-methylenedioxy-2'-methoxystilbene

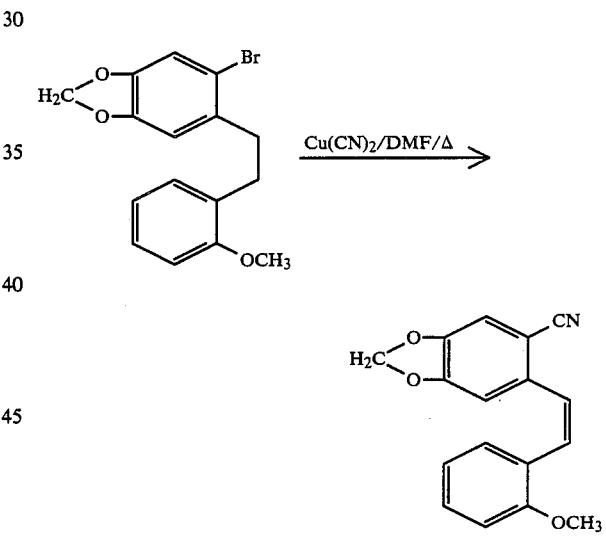

A mixture of 3 g. of the predried stilbene bromide, 4 g. cupric chloride and 30 ml. dimethylformamide is boiled under reflux for 8 to 12 hours until bromide is no longer detectable by thin layer chromatography (dichloromethane/petroleum ether 1:2 v/v). After cooling, the reaction mixture is poured into a solution of 4 g. ferric chloride, 1 ml. hydrochloric acid and 10 ml. water and the reaction mixture maintained at 70° C. for 20 minutes. Efficient air extraction apparatus must be employed because of the evolution of hydrogen cyanide. Thereafter, the cooled reaction mixture is extracted 5 times with 40 ml. amounts of chloroform, washed twice with 20 ml. amounts of water and then dried over anhydrous calcium chloride. After removal of the solvent, the residue is recrystallized from ethanol. Yield 2.0 g. (70% of theory).

(e) Hydrolysis of the nitrile to the end product

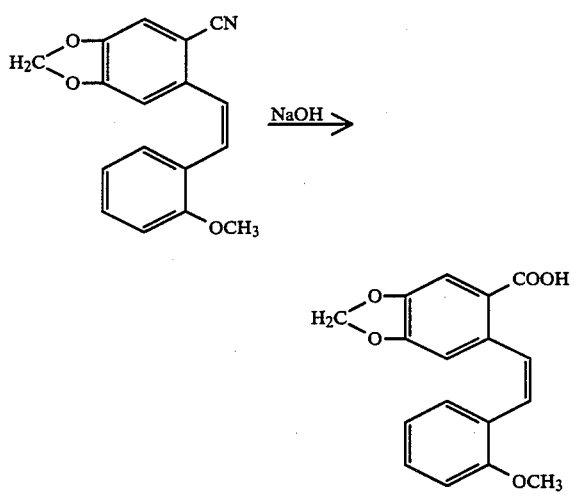

1 g. of the stilbene nitrile is dissolved in 30 to 50 ml. ethanol, with warming, and mixed with a solution of 10 g. sodium hydroxide in 15 ml. water. The reaction mixture is boiled under vigorous reflux until cyanide is no longer detectable by thin layer chromatography, using diethyl ether, this taking 18 to 20 hours. The ethanol is stripped off under a vacuum and 50 to 100 ml. water are added to the residue. The aqueous phase is extracted twice with 30 ml. amounts of diethyl ether and neutralised with 6N hydrochloric acid. The flocculent precipitate obtained mostly remains in the solution as a colloid. The solution is briefly heated and left to stand for 24 hours. The coagulated precipitate is filtered off with suction and recrystallised from ethanol. Yield 0.53 g. (50% of theory).

EXAMPLE 2

Preparation of 1-carboxy-3,4-methylenedioxy-2'-methoxystilbene by conversion of the stilbene bromide into the stilbene acid

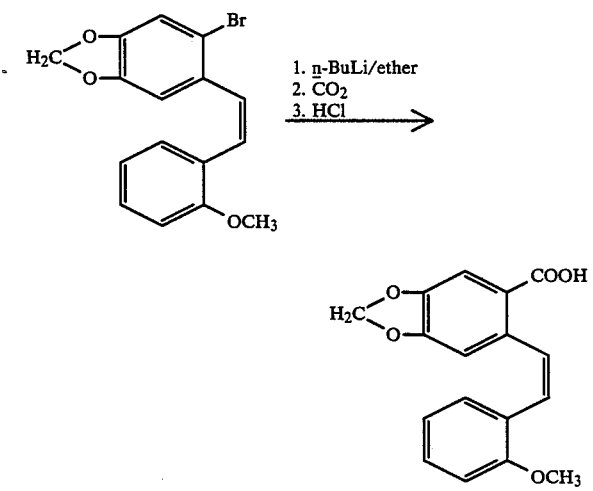

17.44 g. (0.05 mole) of the stilbene bromide are dissolved in 180 ml. anhydrous diethyl ether and cooled to −72° C. under an atmosphere of nitrogen. 40 ml. of a 1.55 molar solution of butyl lithium (0.061 mole) are carefully sprayed into the reaction solution and, after the addition, warmed up to ambient temperature within 1 hour. The solution is then immediately added to solid carbon dioxide and left to react overnight. After the addition of water and phase separation, the aqueous phase is extracted twice with 100 ml. amounts of diethyl ether. The combined aqueous phases are cooled in an ice bath and acidified with concentrated hydrochloric acid. The precipitate obtained is filtered off with suction and neutralized by liberally washing with water. After boiling up two or three times with water for the removal of butyric acid originating from the butyl lithium, the crude product is recrystallised from aqueous ethanol. Yield 9.16 g. (58.7% of theory); m.p. 199.5° C.

The stilbene bromide used as starting materials can be obtained in the manner described in Example 1a–c).

EXAMPLE 3

1-Carboxy-3,4-methylenedioxy-8-methoxyphenanthrene (a) Photochemical conversion of the stilbene derivative into the corresponding phenenthrene derivative

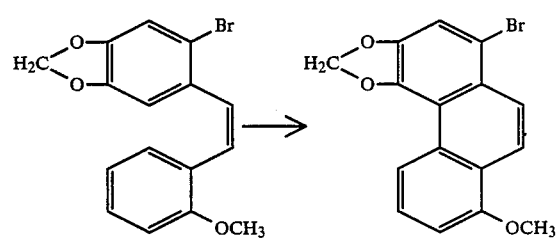

3.3 g. (0.01 mole) cis-stilbene bromide are dissolved in 100 ml. anhydrous 1,2,3,4-tetrahydro-9-fluorenone. This solution is diluted with 1200 ml. anhydrous cyclohexane and mixed with 1.7 g. iodine. The solution is illuminated, while passing in nitrogen, with a laboratory immersion lamp with cooling tube of the type TQ 150 (Hanau) for 12 to 14 days. The reaction is monitored by thin layer chromatography (dichloromethane/petroleum ether (b.p. 30° to 50° C.) 1:2 v/v). The organic phase is shaken out three times with 300 ml. amounts of thiosulphate solution in order to remove excess iodine. After drying over anhydrous magnesium sulphate, the organic phase is evaporated on a rotary evaporator and the crude product obtained is recrystallised from petroleum ether (b.p. 60° to 90° C.). Yield 1.55 g. (47% of theory).

(b) Preparation of 1-cyano-3,4-methylenedioxy-8-methoxyphenanthrene from the phenanthrene bromide Conversion of the phenanthrene bromide into the nitrile:

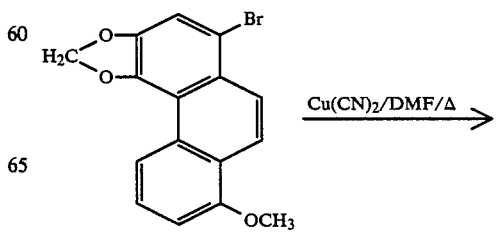

-continued

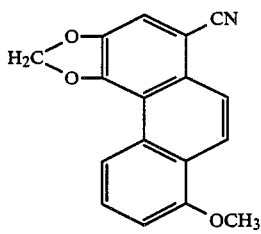

A mixture of 3 g. of predried phenanthrene bromide, 4 g. cupric cyanide and 30 ml. dimethylformamide is boiled under reflux for 8 to 12 hours until bromide can no longer be detected by thin layer chromatography (dichloromethane/petroleum ether 1:2 v/v). After cooling, the reaction mixture is introduced into a solution of 4 g. ferric chloride, 1 ml. hydrochloric acid and 10 ml. water and the reaction mixture maintained for 20 minutes at 70° C., taking care to remove the hydrogen cyanide which is evolved. Thereafter, the cooled reaction mixture is extracted five times with 40 ml. amounts of chloroform, washed twice with 20 ml. amounts of water and dried over anhydrous calcium chloride. Afte removal of the solvent, the residue is recrystallised from ethanol. Yield 2.0 g. (70% of theory); m.p. 215° C.

(c) Hydrolysis of the phenanthrene nitrile to the phenanthrene acid

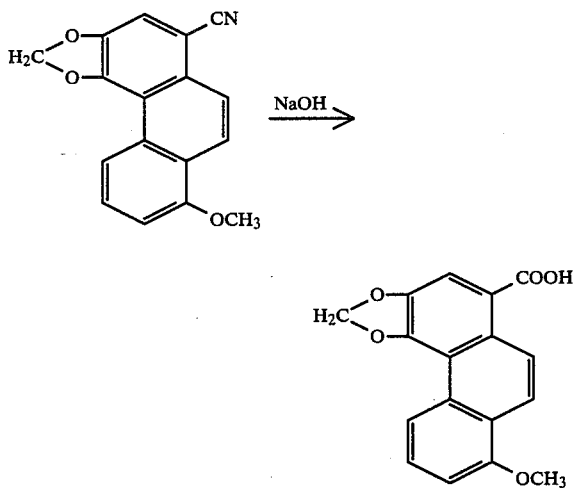

1 g. of the phenanthrene nitrile is dissolved, with warming, in 30 to 50 ml. ethanol and mixed with a solution of 10 g. sodium hydroxide in 15 ml. water. The reaction mixture is boiled under vigorous reflux until cyanide can no longer be detected by thin layer chromatography (diethyl ether), which takes 18 to 20 hours. The ethanol is stripped off under a vacuum and 50 to 100 ml. of water are added to the residue. The aqueous phase is extracted twice with 30 ml. amounts of diethyl ether and neutralised with 6N hydrochloric acid. The flocculent precipitate obtained mostly remains in solution in colloidal form. The solution is heated briefly and then left to stand for 24 hours. The coagulated precipitate is filtered off with suction and recrystallised from ethanol. Yield 0.53 g. (50% of theory).

EXAMPLE 4

Preparation of 1-carboxy-3,4-methylenedioxy-8-hydroxyphenanthrene 1.0 g. 1-carboxy-3,4-methylenedioxy-8-methoxyphenanthrene is melted with 2.0 g. pyridine hydrochloride in an oil bath at 170° C. and maintained at this temperature for 1 hour while gassing with nitrogen. After cooling, the solidified mass is taken up with 10 liters 5% hydrochloric acid and extracted three times with 10 liter amounts of chloroform. The extracts are combined, washed neutral with water and dried by filtering through silanised filter paper (Whatman 1 PS). After evaporation of the solvent at 30° C. on a rotary evaporator, the mixture of starting material and hydrolysate is esterified for separation by boiling under reflux for 3 hours with a mixture of 2.5 liters methanol and 0.1 liter concentrated sulphuric acid. The reaction mixture is then poured into 10 liters of water and the aqueous methanolic phase shaken out three times with 10 liter amounts of diisopropyl ether. The organic solvent, after having been washed several times with water, is extracted with 10 liters of sodium hydroxide solution, the methyl ester of the 8-methoxy compound remaining in the organic phase, whereas the 8-hydroxy compound is transferred into the aqueous phase, with simultaneous hydrolysis of the ester. After washing with fresh diisopropyl ether, the alkaline phase is acidified and shaken out several times with chloroform. The chloroform solution is dried over phase separation paper (Whatman 1 PS) and the solvent stripped off on a rotary evaporator, 1-carboxy-3,4-methylenedioxy-8-hydroxyphenanthrene remaining behind in solid form as a thin layer chromatographically-uniform compound.

Yield 0.714 g. (75% of theory).

Fluorescence: (methanol; $\lambda_{max}$, nm): excitation: 261, 302, 318, 329, 358, 377 emission: 386, 402.

EXAMPLE 5

Preparation of 1-carboxy-3,4-methylenedioxy-8-methoxyphenanthrene by reduction of the nitro group 5 g. Aristolochic acid are dissolved in 1500 ml. 1% aqueous sodium carbonate solution and subsequently filtered into a 5 liter flask. To this clear solution are added 1500 ml. commercially available ammonium polysulphide solution. The reaction mixture is stirred for 2 hours at ambient temperature, using efficient ventilation, and stored overnight in a closed flask. Subsequently 1500 ml. demineralized water are added thereto, followed by acidification by the dropwise addition of 550 ml. concentrated hydrochloric acid, while stirring. The precipitate thereby obtained is filtered off and washed with water. The aqueous phase is extracted with 1500 ml. ethyl acetate. This ethyl acetate phase is used for stirring out the precipitate and this subsequently repeated twice, with stirring, using 1500 ml. amounts of ethyl acetate. The organic phases are combined and washed twice with 500 ml. amounts of water. Subsequently, the ethyl acetate solution is extracted four times with 750 ml. 2% aqueous sodium hydroxide solution. The organic phase is discarded, the aqueous alkaline solution is adjusted to pH 3–4 with concentrated hydrochloric acid and then again shaken out four times with 1000 ml. amounts of ethyl acetate. The combined organic phases are washed three times with 750 ml. amounts of water. The washed organic phase is dried over anhydrous sodium sulphate and subsequently, after filtration, evaporated to dryness in a vacuum at a bath temperature of about 30° C. Yield 3.1 g.; m.p. 285° C. (decomp.). The product can be purified by recrystallization from ethyl acetate.

It will be understood that the specification and examples are illustrative but not limitative of the present invention and that other embodiments within the spirit and scope of the invention will suggest themselves to those skilled in the art.

What is claimed is:

1. Method for treating a disease characterized by depressed macrophage activity or phagocytosis comprising administering to a subject with said disease a therapeutically effective amount of a compound of the formula

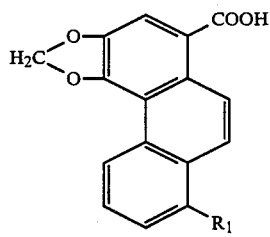

(I)

wherein $R_1$ is hydrogen, hydroxy, methoxy or ethoxy.

2. Method of claim 1, wherein said compound is administered in an amount from 20 mcq/kg of body weight of said subject to 5 mg/kg of body weight of said subject.

3. Method of claim 1, wherein said infectious disease is associated with mycobacterial or pneumococcal infections.

4. Method of claim 1, wherein said infectious disease is associated with depressed phagocytosis.

5. Method of claim 1, wherein said infectious disease is associated with a viral infection.

6. Method of claim 1, wherein said composition is administered intraperitoneally.

* * * * *